United States Patent [19]
Collora et al.

[11] Patent Number: 5,896,692
[45] Date of Patent: Apr. 27, 1999

[54] FREEZE DRIED SCENT LURES

[76] Inventors: Samuel C. Collora; Judith C. Collora, both of Rte. 4, Box 240, Mount Pleasant, Iowa 52641

[21] Appl. No.: 08/926,186

[22] Filed: Sep. 9, 1997

Related U.S. Application Data

[63] Continuation of application No. 08/608,675, Feb. 29, 1996, abandoned.

[51] Int. Cl.$^6$ ................................................. A01N 25/00
[52] U.S. Cl. ..................................................... 43/1; 424/84
[58] Field of Search ....................................... 43/1; 424/84

[56] References Cited

U.S. PATENT DOCUMENTS

| | | | |
|---|---|---|---|
| 2,959,354 | 11/1960 | Beck | 239/36 |
| 3,046,192 | 7/1962 | Bilyeu | 43/1 |
| 3,615,727 | 10/1971 | Starke | 422/33 |
| 3,901,655 | 8/1975 | Shukla et al. | 436/8 |
| 3,912,655 | 10/1975 | Shukla et al. | 436/162 |
| 4,229,477 | 10/1980 | Shelley et al. | 514/655 |
| 4,305,969 | 12/1981 | Munk | 426/580 |
| 4,308,202 | 12/1981 | Fujii et al. | 530/331 |
| 4,465,624 | 8/1984 | Chiba et al. | 530/395 |
| 4,785,765 | 11/1988 | Campbell et al. | 119/417 |
| 4,806,274 | 2/1989 | Crouse et al. | 252/548 |
| 4,944,940 | 7/1990 | Christenson, II | 424/84 |
| 5,186,118 | 2/1993 | Stinson | 116/214 |
| 5,194,280 | 3/1993 | Palermiti | 426/330.5 |
| 5,283,197 | 2/1994 | Robins | 436/87 |
| 5,303,496 | 4/1994 | Kowalkowski | 43/1 |
| 5,369,903 | 12/1994 | Cox | 43/1 |
| 5,565,111 | 10/1996 | Newman | 210/774 |
| 5,595,137 | 1/1997 | Delmonte | 116/264 |
| 5,672,342 | 9/1997 | Bell | 43/1 |
| 5,698,111 | 12/1997 | Newman | 424/84 |

*Primary Examiner*—Michael J. Carone
*Assistant Examiner*—Darren Ark
*Attorney, Agent, or Firm*—Zarley, McKee, Thomte, Voorhees & Sease

[57] ABSTRACT

A scent lure for hunting is produced from collected animal urine which is freeze dried so as to yield a powdered urine product. The freeze dried scent lure may be used by hunters with or without rehydration. The freeze dried product is free from preservatives and maintains the natural chemical composition of the urine. Handling of the freeze dried scent lure is greatly simplified, as compared to liquid urine lures. Glands and glandular secretions may be blended with the urine prior to freeze drying. The freeze dried scent lure maintains its freshness and has an indefinite shelf life.

13 Claims, No Drawings

FREEZE DRIED SCENT LURES

This is a continuation of application Ser. No. 08/608,675 filed on Feb. 29, 1996 now abandoned.

BACKGROUND OF THE INVENTION

Scents and lures have been used by hunters and trappers to aid them in attracting their quarry for thousands of years. In the past century, the manufacture and sale of lures, including scented lures, has become a commercial enterprise. More specifically, scented lures have become popular with hunters to attract deer or other game animals to a hunting site. Particularly, doe urine with estrus will attract a buck looking to mate. Since bucks are territorial, urine from another buck will attract a buck to protect its territory. There are many applications for the lures. For example, the scented lure is sprinkled on the ground.

Scented lures are generally urine based, and thus are in a liquid form. These conventional fresh liquid urine lures have a limited refrigerator life of approximately three months. Some manufacturers add preservatives to increase the shelf life of the product. However, then the product is no longer a natural product. Also, since the deer hunting season is normally limited to the fall, collection of the fresh deer urine is seasonal, due to the limited refrigerator life of the lure product. Collection of estrus urine and buck rut urine is limited to the breeding cycle of the deer. Thus, production of a scented lure using these special urines is even more limited in time. These liquid lures also present handling problems, both at the retail location and in the field. Another disadvantage of fresh liquid urine scent lures is the need to refrigerate the product, so as to retard bacterial growth, and thereby maintain product freshness. Freeze drying has been used in the medical industry for the preservation of drugs and serums.

Accordingly, a primary objective of the present invention is the provision of freeze dried scent lures for hunting or trapping.

Another object of the present invention is a method of making scent lures using a freeze drying process.

A further objective of the present invention is the provision of an improved scent lure which is freeze dried so as to produce a powdered product having a substantially unlimited shelf life.

Still another objective of the present invention is the provision of a freeze dried scent lure which is economical to manufacture and effective in use.

These and other objectives will become apparent from the following description of the invention.

SUMMARY OF THE INVENTION

The improved scent lure of the present invention is a freeze dried urine-based powdered product. The product is made by collecting fresh urine from a species of the animal to be hunted or trapped, and then freeze drying the collected urine to produce a powdered urine product. The urine may be frozen prior to freeze drying so as to minimize the time required for freeze drying. Natural additives, such as glands and glandular secretions may be added to the urine prior to freeze drying. A hunter or trapper may use the freeze dried scent lure in the powdered state, or may rehydrate the lure using distilled water, spring water, snow, or fresh urine.

DETAILED DESCRIPTION OF THE INVENTION

The improved scent lure of the present invention constitutes a urine based powdered product produced from freeze drying animal urine. This scent lure is useful to hunters or trappers who wish to attract an animal, such as a whitetail deer or an elk, to a specific hunting site. Scent lures may be useful for other animals, including but not limited to moose, bear, and raccoon.

Urine from the species of animal to be hunted or trapped is collected by known methods. For example, deer may be herded into stalls in a barn or other structure having slatted floors. The urine passes through the slatted floors into collection troughs beneath the floor. The slatted floors prevent feces, mud and other contaminates from passing through to the urine collection troughs, thereby minimizing bacterial contamination of the urine. Since urine is sterile when it is eliminated from the animal, it is desirable to prevent or minimize contamination of the urine. The urine may be filtered to remove the few solid materials which pass through the slatted floors. The urine is then collected in trays or other suitable containers.

It is preferable to segregate doe urine from buck urine. Thus, the does are typically herded into a different stall or pen than the bucks. The bucks are also normally isolated in individual stalls to prevent fighting during the rut, and for the safety of the animals and human handlers. Further refinement of the collection process is desirable during the breeding season. For example, estrus urine collected from a doe in heat may be blended with fresh whitetail doe urine to produce an enhanced scented lure. Similarly, urine collected from bucks during the rut also is useful as a special scented lure which attracts bucks who believe that another buck is trespassing on its territory.

The collected urine is preferably frozen prior to the start of the freeze drying process. This pre-freezing of the urine reduces the time required for freeze drying.

A commercial freeze drying unit is used to freeze dry the urine. One suitable freeze dryer is sold by FTS Systems, Inc., in Stone Ridge, N.Y. under the trademark Dura-Dry. The optimum freeze drying temperature for deer urine is approximately $-60°$ C. The freeze dryer has an upper vacuum chamber and a lower condensing chamber. The freeze dryer is prechilled for at least four hours prior to the introduction of the urine, such that the vacuum chamber is approximately $-30°$ C. and the condensing chamber is $-85°$ C. The urine is then placed into the vacuum chamber of the freeze dryer, and the dryer door is closed so as to seal the dryer. The vacuum pump of the freeze dryer is actuated and the unit runs for approximately 12 hours. Then, the temperature for the vacuum chamber is set at $0°$ C., and the machine is left to run for 24 hours. The vacuum chamber temperature is again reset to $25°$ C. and the machine runs for another 24 hours so that the moisture is driven out of the urine to produce a powdered urine product. When the urine reaches a temperature of $+25°$ C. the product is allowed to set for 4 hours, then atmospheric pressure is allowed back into the vacuum chamber. Then the product can be packaged.

The freeze drying process maintains the chemical composition of the urine, and retains the original structure, chromosomes, cell count and hormones. No preservatives are added to the urine. If desired, glandular secretions from the animal, or ground up glands may be added to the urine prior to freeze drying. For example, buck tarsal glands and tarsal secretions may be added to the urine. Other glands may be blended with the urine to produce a glandular lure for use in making mock scrapes to attract a buck.

The freeze dried powdered urine product may be packaged after freeze drying in any convenient package.

Alternatively, the collected liquid urine may be placed into bottles, without caps, and the uncapped bottles placed directly into the upper vacuum chamber of the freeze dryer so that the urine is freeze dried in the bottles. Upon completion of the freeze drying process, the bottles may be capped for shipping and storage.

The freeze drying process produces a powdered scent lure which will maintain freshness indefinitely. The freeze dried lure may be used with or without rehydrating. For example, the powdered urine may be sprinkled dry onto a buck scrape to be rehydrated by dew overnight, or the buck may rehydrate the powdered product. A more potent scent lure may be achieved by rehydrating with fresh liquid deer urine. Also, distilled water, spring water, or melted snow may be used to rehydrate the freeze dried urine. Preferably, chlorinated tap water should not be used to rehydrate the product, since such water kills the pheromones which are preserved in the freeze dried state.

The freeze dried scent lure eliminates the need to refrigerate, which is necessary for liquid scent lures to minimize and retard bacterial growth. Handling of the freeze dried packaged product is simplified, since the potential for spillage of liquid is eliminated. When the powdered urine is rehydrated, it is as fresh as the day it was freeze dried. Also, use of the freeze dried lure in the field by hunters is simplified, since it is easier to handle a solid powder product than a liquid urine lure.

From the foregoing, it can be seen that at least all of the stated objectives are achieved by the present invention.

What is claimed is:

1. A scent lure for use in hunting or trapping, comprising:
   animal urine reduced to a powder by freeze drying;
   said powder including all of the odoriferous ingredients found in the animal urine.

2. The scent lure of claim 1 further comprising glandular secretions blended with the urine.

3. The scent lure of claim 1 wherein the urine is free of preservatives.

4. A scent lure for hunting or trapping, comprising:
   animal urine collected from a species to be hunted;
   the urine being freeze dried into a powdered product wherein said product includes all of the odoriferous ingredients found in the collected animal urine.

5. The scent lure of claim 4 wherein the powdered product is rehydrated at a hunting site.

6. The scent lure of claim 4 further comprising glandular secretions blended with the urine.

7. The scent lure of claim 4 further comprising animal glands blended with the urine.

8. A scent lure for hunting or trapping, comprising:
   animal urine collected from a species to be hunted;
   the urine being freeze dried into a powdered product;
   said urine being substantially free of additives or preservatives,
   said product including all of the odoriferous ingredients found in the animal urine.

9. A method of making a scent lure for hunting or trapping, consisting essentially of:
   collecting a quantity of urine from a species of animal to be hunted while preventing feces from entering the collected urine; and
   placing the urine into a freeze dryer until the moisture is driven out of the urine to produce a powdered urine product.

10. The method of claim 9 wherein the scent lure is made without preservatives.

11. The method of claim 9 further comprising freezing the collected urine prior to the step of placing the urine into the freeze dryer.

12. The method of claim 9 further comprising blending glandular secretions with the collected urine prior to the step of placing the urine into the freeze dryer.

13. A method of making a scent lure for hunting or trapping, consisting essentially of:
   collecting a quantity of urine from a species of animal to be hunted while preventing feces from entering the collected urine; and
   placing the urine into a freeze drier at a temperature of approximately −60° C. until the moisture is driven out of the urine to produce a powdered urine product.

* * * * *